(12) United States Patent
Müller

(10) Patent No.: US 8,130,901 B2
(45) Date of Patent: Mar. 6, 2012

(54) LIMITING AN X-RAY BEAM IN CONNECTION WITH DENTAL IMAGING

(75) Inventor: Timo Müller, Espoo (FI)

(73) Assignee: Planmeca Oy, Helsinki (FI)

( * ) Notice: Subject to any disclaimer, the term of this patent is extended or adjusted under 35 U.S.C. 154(b) by 127 days.

(21) Appl. No.: 12/531,747

(22) PCT Filed: Mar. 11, 2008

(86) PCT No.: PCT/EP2008/052864
§ 371 (c)(1),
(2), (4) Date: Sep. 17, 2009

(87) PCT Pub. No.: WO2008/113715
PCT Pub. Date: Sep. 25, 2008

(65) Prior Publication Data
US 2010/0119036 A1      May 13, 2010

(30) Foreign Application Priority Data
Mar. 19, 2007   (FI) ...................................... 20070221

(51) Int. Cl.
*A61B 6/14*    (2006.01)
*G21K 1/02*    (2006.01)
(52) U.S. Cl. ............................ 378/38; 378/147; 378/148
(58) Field of Classification Search ................. 378/38, 378/147–148, 156–158, 161, 210
See application file for complete search history.

(56) References Cited

U.S. PATENT DOCUMENTS

| | | | |
|---|---|---|---|
| 4,783,793 A | 11/1988 | Virta et al. | |
| 5,058,147 A | 10/1991 | Nishikawa et al. | |
| 5,086,444 A * | 2/1992 | Bartmann | 378/152 |
| 5,991,362 A * | 11/1999 | Jones | 378/152 |
| 6,148,062 A * | 11/2000 | Romeas | 378/156 |
| 6,289,074 B1* | 9/2001 | Arai et al. | 378/4 |
| 7,336,768 B2* | 2/2008 | Ogawa | 378/156 |
| 2009/0022270 A1* | 1/2009 | Yoshimura et al. | 378/19 |

FOREIGN PATENT DOCUMENTS

| | | |
|---|---|---|
| DE | 3236082 | 3/1984 |
| DE | 3930022 | 3/1990 |
| EP | 0236790 | 9/1987 |
| EP | 0485742 | 5/1992 |
| EP | 1684637 | 8/2006 |
| FI | 894310 | 3/1990 |
| WO | 2002/097827 | 12/2002 |
| WO | 2005/048845 | 6/2005 |
| WO | 2006/108920 | 10/2006 |
| WO | 2006/109808 | 10/2006 |

* cited by examiner

Primary Examiner — Anastasia Midkiff
(74) Attorney, Agent, or Firm — Cozen O'Connor

(57) ABSTRACT

The present invention relates to limiting an x-ray beam used in connection with dental extra oral imaging by a plate mechanism (1) arranged to be operated by a drive mechanism including an actuator (3) arranged to move at least one plate element (2, 3) comprised in the mechanism (1). The plate mechanism (1) includes at least a first and a second plate element (2, 3) which include at least a first slot (12) and a second slot (13), respectively, and said drive mechanism is arranged to directly or indirectly move said first plate element (2) independently of location of said second plate element (3) and said second plate element (3) is arranged to be moved as dependent on the movements of said first plate element (2) only.

18 Claims, 4 Drawing Sheets

LIMITING AN X-RAY BEAM IN CONNECTION WITH DENTAL IMAGING

FIELD OF THE INVENTION

The present invention relates to methods and apparatus for limiting an x-ray beam in connection with dental extra oral imaging.

RELATED PRIOR ART

Dental radiography has been traditionally considered including so-called intraoral imaging, which typically means imaging individual or a few teeth, extra oral imaging the most common imaging modes of which being so-called panoramic imaging, which means producing a layer image, i.e. a tomogram of the dental arch, and so-called cephalometric imaging, which typically means producing a transillumination image of the area of an entire skull. Often the same dental imaging apparatus is used for taking both panoramic and cephalometric images. Recently, use of the dental panoramic x-ray apparatus has expanded for producing various special images of different parts of the dental arch and even for 3D imaging.

When using the same x-ray apparatus for more than one medical imaging purpose, it may be necessary to be able to limit the x-ray beam according to the requirements of the imaging mode in question. In other words, in view of radiation hygiene, one must be able to limit the beam to different shapes and/or sizes. To this end, prior art dental panoramic x-ray imaging apparatuses, for example, include various kinds of adjustable and/or replaceable plate constructions, i.e. collimators.

Collimators according to prior art may constitute one or more plates and/or the plates may include a number of different apertures. Typically, when a new exposure is to be made using a different imaging mode than that used in the previous one, the x-ray beam must be limited correspondingly by using an aperture of different shape and/or size. However, the space available in imaging apparatus often imposes certain restrictions as to the number of different apertures that can be arranged in a single plate as well as to the number of plates as such that can be arranged into the apparatus. In case the plates are arranged releasably connected and changeable, the arrangements needed allowing the replacement also involve certain problems regarding convenience of use of the apparatus. Further, a storage system must be arranged for the plates that are not in use at a given time.

One prior art solution is to use e.g. a so-called four-plate-type collimator for limiting the beam both vertically and horizontally, in which each of the plates are driven by a separate actuator. The construction allows various beam sizes and forms to be provided for various imaging modes. However, the use of several actuators leads to increased cost of the construction, to complex electronics for controlling the actuators and to a certain space requirement for the actuators.

Another kind of prior art plate mechanism is disclosed in Finnish patent application 894310, claiming priority from Japanese utility model 63-119939. This mechanism comprises two plate elements, which can be driven relative to each other in the horizontal direction individually by their respective actuators. The plate elements are provided with apertures of different sizes. The overall aperture limiting the beam is defined by the overlapping position of the apertures. As in the case of the four-plate mechanism, the two actuators of this construction require a certain amount of space within the apparatus and respective control electronics.

Further prior art plate mechanisms are disclosed in German patent publication 3236082 and WO patent publication 02/097827. Both of these disclose a construction in which the aperture limiting the beam is formed between two movable plate elements, driven by a single actuator. Even though space is saved in the imaging apparatus by using a single actuator, contrary to e.g. the four-plate construction discussed above, the space occupied by the plate elements arranged side-by-side is correspondingly wider. Further, regarding the construction of DE 32 36 082, it enables a synchronized movement of the plates limiting the beam only and also offers no means to adjust the location of the aperture to be formed, only its width. Yet another aspect is that when a beam is limited by two plate elements arranged next to each other, should the aperture be adjustable e.g. in two perpendicular directions, two such pairs of plate elements would be needed which, obviously, would lead to an even greater space requirement.

SUMMARY OF THE INVENTION

The object of the current invention is to reach new solutions in view of the problems discussed above, especially in view of complexity and space requirements of the collimator constructions. The method and apparatus of the invention are characterized by at least first and second movable plate elements including first and second respective slots which overlap to form a beam-limiting aperture wherein the first plate element is moved by an actuator of a drive mechanism independently of the location of the second plate element whereas the second plate element is moved solely by and dependent on the movements of the first plate element.

The current invention provides the advantage of making it possible to adjust the shape of the aperture limiting an x-ray beam of an extra oral imaging apparatus in two dimensions at a reasonable cost by using a single collimator construction and one actuator only. By the combined use of only one actuator, to operate the overlapping plate construction of the invention, the space the construction occupies in the imaging apparatus may be arranged to be reasonable yet x-ray beams of different shapes in two dimensions may be formed without having to arrange the plate elements replaceable. Reasonable number of components only is needed to realize the construction.

BRIEF DESCRIPTION OF THE DRAWINGS

In the following, the invention will be described in more detail with the help of its certain preferable embodiments with reference to the attached figures. Of the figures.

DESCRIPTION OF THE PREFERRED EMBODIMENTS

Figure 1A:
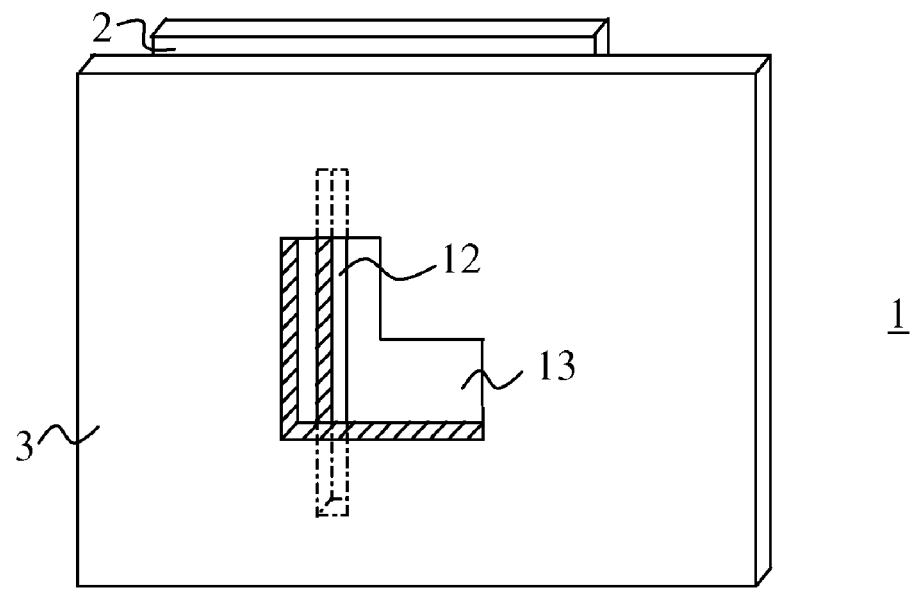
FIG. 1a presents a front view of plate elements of a first plate mechanism according to the invention.
Figure 1B:
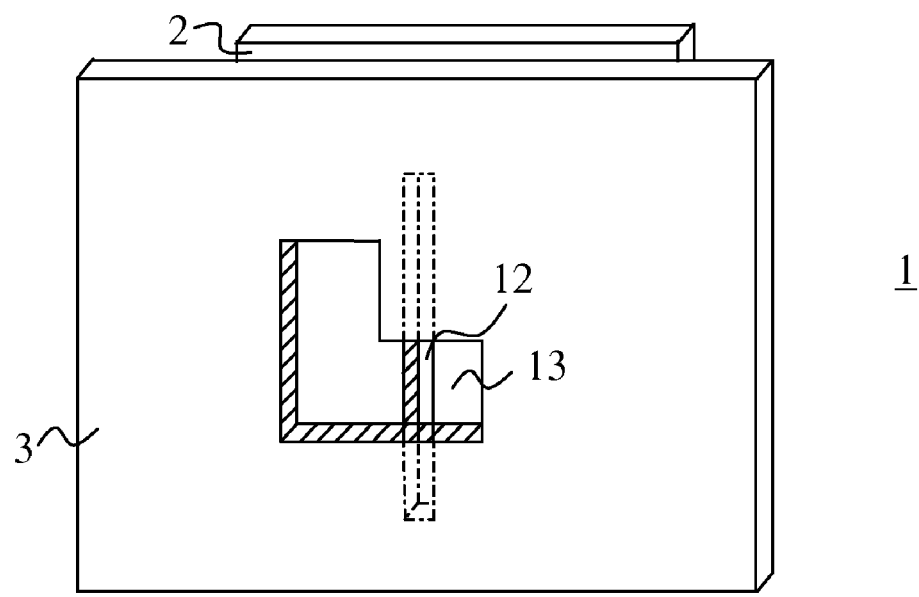
FIG. 1b presents a front view of the plate elements of the first plate mechanism of FIG. 1a, the plate elements being positioned in a different respective position.

FIGS. 1a and 1b present a front view of plate elements of one embodiment of the invention. These figures show the plates only, a drive mechanism of the plate mechanism according to the invention will be discussed further below.

The plate mechanism (1) according to FIG. 1 comprises a first plate element (2) and a second plate element (3). The first plate element (2) includes a first slot (12) and the second plate element (3) includes a second slot (13). The first slot (12) of the first plate element (2) is arranged to be rectangular and its horizontal dimension to be substantially smaller than its vertical dimension. The second slot (13) is arranged to have two portions of different heights. The construction is designed to make possible arranging the slots (12, 13) of the first and second plate elements (2, 3) to lie on top of each other, by arranging at least portions of the plate elements (2, 3) movable on different planes. The first slot (12) is arranged to be at least as high as is the distance from the lowest point of the second slot (13) to the highest point of the second slot (13). The second slot (13) is arranged to be at least as wide as the first slot (12)—or, actually, each portion of the second slot (13) having a constant height is arranged to be at least as wide as the first slot (12). When an x-ray beam is directed towards this collimator construction, the form of the x-ray beam having passed the construction will be defined by the width of the first slot (12) and by the height of the second slot (13).

FIG. 1b presents a front view of the plate mechanism of FIG. 1a with the plate elements (2, 3) in different respective positions. Again, the locations of the slots (12, 13) is such that the width of the x-ray beam having passed the construction will be defined by the width of the first slot (12) and the height by the second slot (13), now by another portion of the second slot (13) than in FIG. 1a. As a result, the x-ray beam will be lower than when the plate elements (2, 3) are position according to FIG. 1a.

Figure 2A:
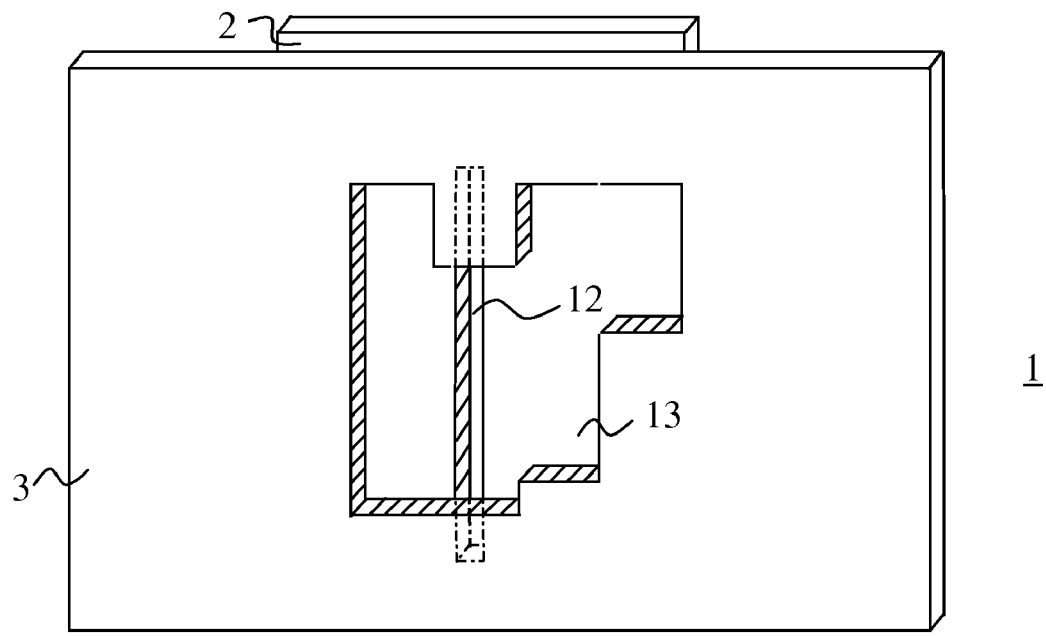
FIGS. 2a and 2b present front views of plate elements of two other embodiments of the plate mechanism according to the invention.
Figure 2B:
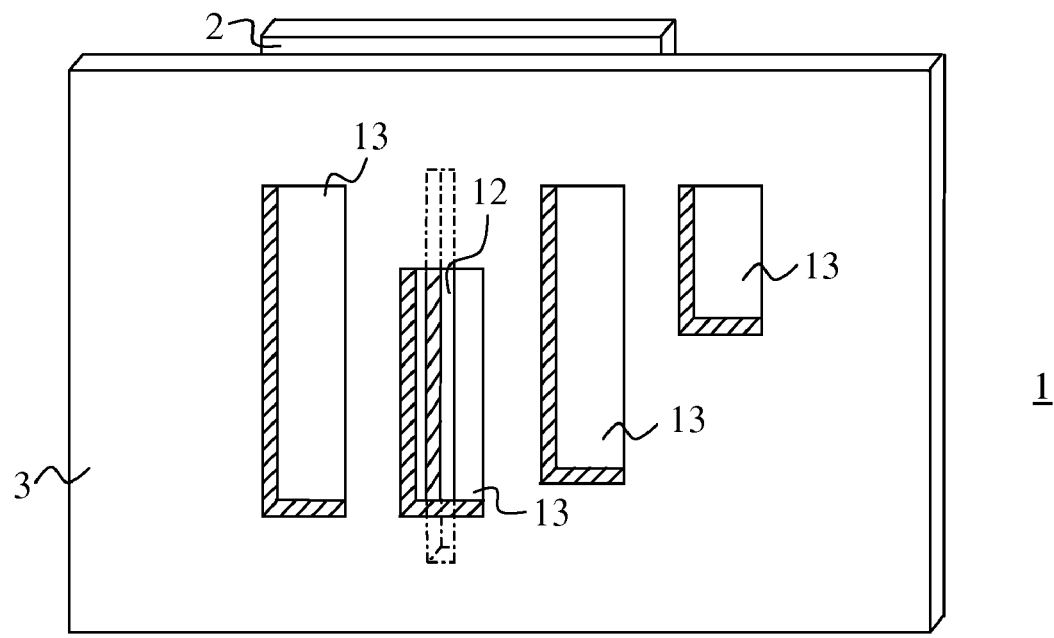

As shown in FIGS. 2a and 2b, the second plate element (3) may be arranged to include a second slot (13) having many portions of different heights as well as portions whose lowest and highest points are on different horizontal levels. Further, the second plate element (3) may be arranged to include two or several separate slots (13) of different heights and/or slots (13) being located at different horizontal levels—in view of FIGS. 2a and 2b, as if corresponding the portions of different heights of the somewhat complex single slot (13) of FIG. 2a. Here, again, the first slot (12) is arranged to be at least as high as is the distance from the lowest point of the second slot (13) to the highest point of the second slot (13)—or from the lowest point of the slot (13) located lowest on the second plate element (3) to the highest point of the slot (13) located highest on the second plate element (3). Also, again, the second slot (13) is arranged to be at least as wide as the first slot (12)—or, actually, each portion of the second slot (13) having a constant height is arranged to be at least as wide as the first slot (12). Incase there is more than one slot (13) in the second plate element (3), the same dimension criteria apply for each of the slots (13).

In view of space occupied by the second plate element (3), the embodiment of only one slot (13) is obviously preferable. In case more than one slot (13) is to be arranged in the second plate element (3), it is preferable to arrange them quite close to each other. In this respect, the embodiment shown in FIG. 2b is drawn basically just to demonstrate separation of the various portions of the second slot (13) of FIG. 2a; according to a preferable embodiment of the invention, spacing of the slots (13) would be tighter.

As will be discussed in more detail below in view of FIGS. 3a and 3b, the first and second plate elements (2, 3) of the plate mechanism (1) of the invention are arranged movable with respect to each other such that at least portions of the plate elements (2, 3) move on different planes thus allowing an overlapping positioning of the first and second slots (12, 13). In the embodiments shown in the FIGS. 1-3, the plate elements (2, 3) are arranged as flat and movable on different planes in their entirety, but it is also possible to arrange the plate elements (2, 3) to have such a construction that only parts of the plate elements (2, 3) move on different planes, to allow for an overlapping positioning of the slots (12, 13).

Above, the essential aspect of the invention of overlapping positioning of the slots limiting the beam has been discussed. Another essential feature of the invention regarding the drive mechanism of the plate construction (1) will now be discussed with respect to FIGS. 3a and 3b, showing yet another embodiment of the invention.

Figure 3A:
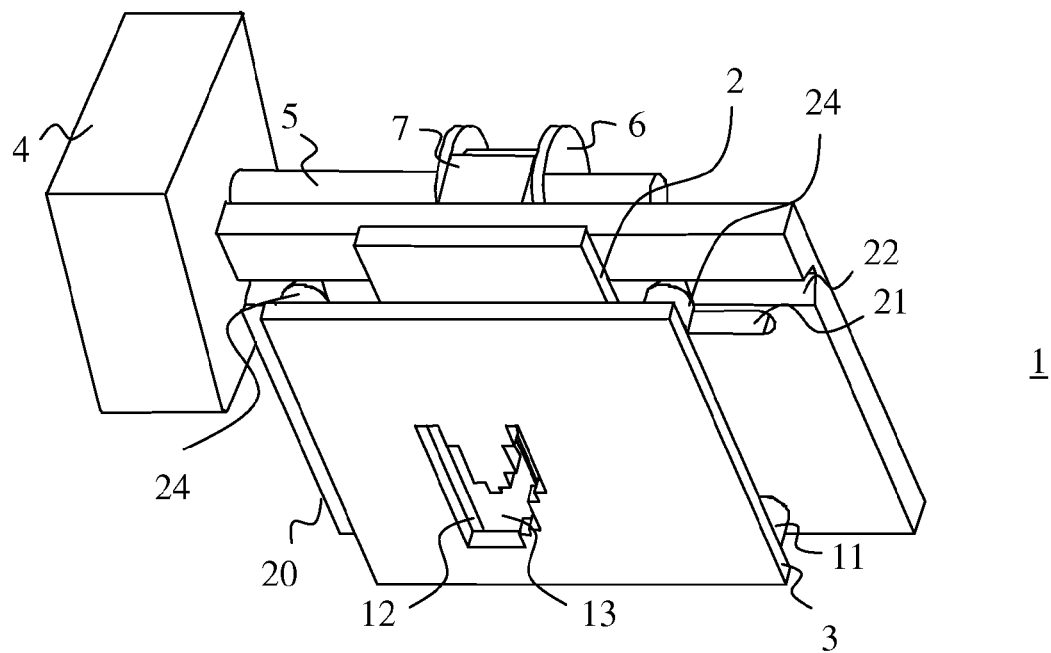
FIGS. 3a and 3b present axiometric front and back views of yet another plate mechanism according to the invention and FIG. 4 presents typical dental extra oral x-reimaging apparatus in which the plate mechanism according to the invention is primarily designed to be used.
Figure 3B:
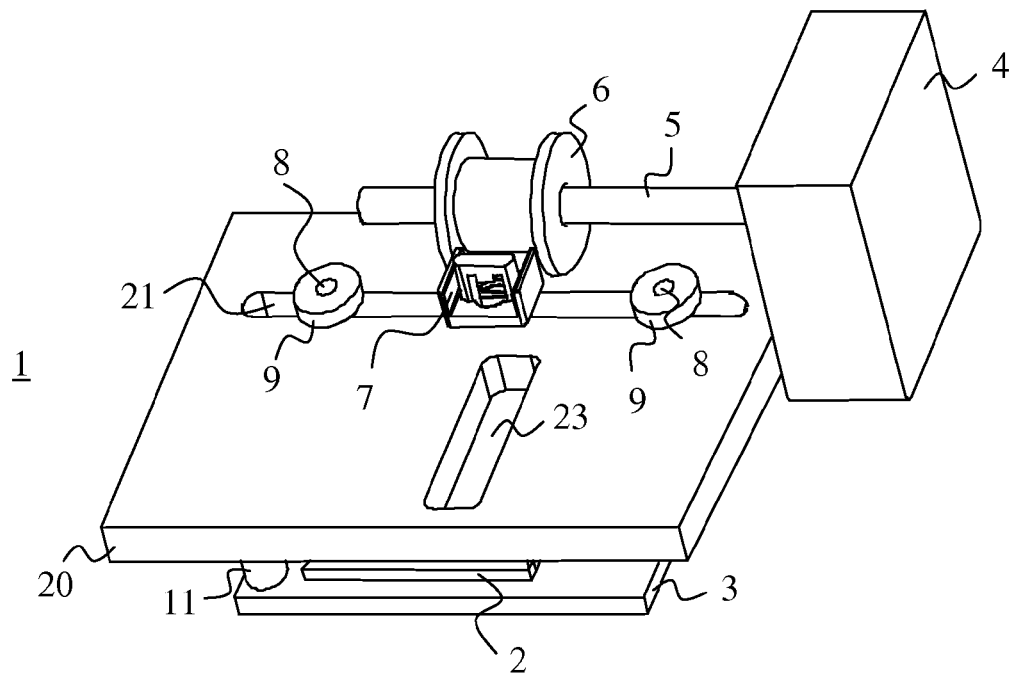

The first and second plate elements (2, 3) of FIGS. 3a and 3b are basically like those in FIGS. 1-2, the only difference being in the more complex shape of the second slot (13) of the second plate element (3). The basic components of the drive mechanism of FIGS. 3a and 3b include an actuator (a motor) (4), a drive screw (5) and a nut (6) arranged in fixed connection with the first plate element (2) via a connection element (7), which goes through an elongated hole (21) arranged in a frame element (20) that supports the plate construction (1). The second plate element (3) is also supported on the frame element (20) by pegs (8), which extend through the same elongated hole (21). The frame element (20) further includes a guide groove (22), along which matching elements (24), arranged both to the first and second plate elements (2, 3), are arranged to slide (matching elements of the first plate element not being visible in the FIGS. 3a and 3b). At the ends of the pegs (8) of the second plate element (3) which extend through the elongated hole (21), locking elements (9) are arranged, as well as near the lower edge of the second plate element (3) a block (11) of a desired dimension for keeping the plate elements (2, 3) at a desired distance from each other. The frame element (20) also includes an aperture (23) for the x-rays generated at the radiation source to go through. The constructions which support the plate elements (2, 3) on the frame element (20) may include e.g. springs to keep the constructions table yet at the same time not to cause such an amount of friction between the guide groove (22) and the matching elements (24) that the plate elements (2, 3) couldn't slide along the guide groove (22).

An essential feature of the plate construction according to the invention, in view of those embodiments of it shown in FIGS. 1-3, is that the second plate element (3) can be driven to a desired position within the operation range of the plate mechanism by using the single actuator (4) of to the construction, said actuator (4) being primarily arranged to move the first plate element (2) by the drive construction of the plate mechanism (1). The idea is to arrange the construction such that when moving the first plate element (2) towards either end of its operation range, at some stage during such a movement the plate elements (2, 3) will meet, directly or via some construction arranged for this purpose, after which any further movement of the first plate element (2) in that direction will cause the second plate element (3) to move in that same direction, too.

Then, further, another essential aspect of the construction is to include such a range within its operation range that, when changing the direction of movement of the first plate element (2) back towards the end opposite to the end towards which it was moving, the contact between the first and second plate elements (2, 3) will be broken and only the first plate element (2) will be moving. In other words, when the direction of movement of the first plate element (2) is changed, when having been in director indirect contact with the second plate element (3), there is always a distance within the operation range of the system within which the first plate element (2) will move alone, i.e. without moving the second plate element (3), prior to the first plate element (2) again meeting the second plate element (3), or some construction being in contact with the second plate element (3), and starting to move the second plate element (3), now in the opposite direction. Thus, the second plate element (3) can never move independently of the movement of the first plate element (2), whereas the first plate element (2) can move both independently without moving the second plate element (3) as well as such that it moves the second plate element (3). In reference to FIG. 3b, when the locking elements (9) of the pegs (8) are arranged of a distance further apart from each other than is the dimension of the first plate element (2) in the direction of movement of the first plate element (2), the construction will function as discussed above.

A construction according to the invention makes it possible to first drive the second plate element (3) to a desired position within the operation range of the mechanism, in order to arrange the second slot (13) of the second plate element (3) to a desired position, after which the direction of movement of the first plate element (2) is reversed to drive the first slot (12) of the first plate element (2), now moving alone, to its desired position with respect to the position of the second plate element (3) to form an aperture which then will be defined by the overlapping slots (12, 13) of the first and second plate elements (2, 3). In reference to the embodiments of the FIGS. 1-3, considering the dimensions the first and second plate elements (2, 3) are arranged to be moved, on different parallel planes, this functionality is reached by arranging said second plate element (3) to be wider than said first plate element (2) and said first plate element (2) to be moved within the width covered by the second plate element (3).

Now, considering the construction shown in FIGS. 3a and 3b, when the drive screw (5) is rotated by the actuator (4), the nut (6) moves axially on the drive screw (5) and thus also moves the first plate element (2) being fixed to the nut (6) by the connecting element (7). The distance between the pegs (8) supporting the second plate element (3) is arranged to be greater than the width of the first plate element (2) so that, depending on the respective positions of the first and second plate elements (2, 3), either the first plate element (2) will move alone or it will also move the second plate element (3)—towards that end of the elongated opening (21)/the guide groove (22) the first plate element is moving. In this construction, the second plate element (3) will begin to move when an edge of the fist plate element (2) meets either one of the pegs (8) (the locking elements (9)) being fixed to the second plate element (3) but, obviously, there are a number of other kinds of constructions by which the same function may be achieved. The ends of the operation range of the plate construction (1) may be defined by the ends of either the elongated slot (21) or the guide groove (22), or by both, for example. The distance the first plate element (2) is arranged to be moved corresponds at least the width of a single second slot (13) of the second plate element (2), or the distance between the outermost slots (13) of the second plate element (3).

Above, a construction has been disclosed where the first plate element (2), basically defining position of the beam limited by the construction, is driven by the actuator (4) and the second plate element (3) via the movements of the first plate element (2). In principal, a contrary arrangement would be possible as well, but since correct positioning of the beam is basically more critical than a precisely exact height of it, a preferable alternative is to arrange the actuator (4) to directly drive specifically that plate element which defines position of the beam.

By the construction according to FIGS. 3a and 3b, rectangular x-ray beams can be created having a width defined by the first slot (12) of the first plate element (2) and the height and the horizontal position defined by the second slot (13) of the second plate element (3). Various kinds of such x-ray beams are needed e.g. in such dental radiology being based on scanning imaging techniques. For example, in view of panoramic imaging scan of dental arcs of adults on the first hand and children on the second, slots (13) having heights of about 26 mm and about 22 mm, respectively, may be arranged in the second plate element (3). Further, rectangular slots extending about 14 mm from the highest horizontal level of that of the slot arranged for panoramic imaging for adults may be arranged in view of panoramic scan of the dental arch of the upper jaw only, and a corresponding slot in view of imaging the dental arch of the lower jaw. Respectively, corresponding slots may be arranged also in view of imaging the upper and lower jaws of children, and e.g. one in view of a panoramic scan excluding the jawbone.

Obviously, the scope of the current invention is not limited to specifically those forms and respective dimensions of apertures creatable by the slots shown in FIGS. 1-3, even though already by e.g. such a collimator construction shown in FIGS. 3a and 3b, one is able to cover a number of typical x-ray beam sizes and beam positions typically used in a dental extra oral x-ray apparatus. Alternative or additional slot forms may be e.g. triangular ones enabling stepless adjustment of a dimension of the aperture, one having a height suitable for cephalometric imaging (imaging of the whole skull) and apertures of more complex forms than a rectangle or a triangle, such as ones having at least one curved edge. Further, more than one slot may be arranged either to the first or second plate element, or to both of them, there may be slots arranged not only next to each other but also on top of each other, and such a construction is also possible where the second plate element includes only one slot and the first plate element a slot or slots of various heights. A plate element may also be arranged to include both a more complex type aperture such as shown in FIGS. 2a and 3a, for example, and additionally one or more bare rectangles, for example. Further, either the first or the second plate element may be arranged to be the one being closer to the x-ray source.

The plate construction according to the invention preferably comprises a means for detecting position of the first plate element within its operation range, even though the construction can be used even without such means as well by e.g. always starting a positioning-drive-sequence of the plate elements by driving the plates to an end of the operation range of the construction. This done, one will always know where the plate elements are positioned upon starting positioning of the plates, and by using e.g. a stepping motor one will be able to keep track of whereto the elements have been moved.

Control system for the plate construction preferably includes pre-defined drive sequences for the plate elements, to be used in connection with typical imaging modes applied by the imaging apparatus. In addition, the user interface may include the option of driving the actuator 'manually' as well, for fine-tuning purposes of positioning the beam, for example.

Figure 4:
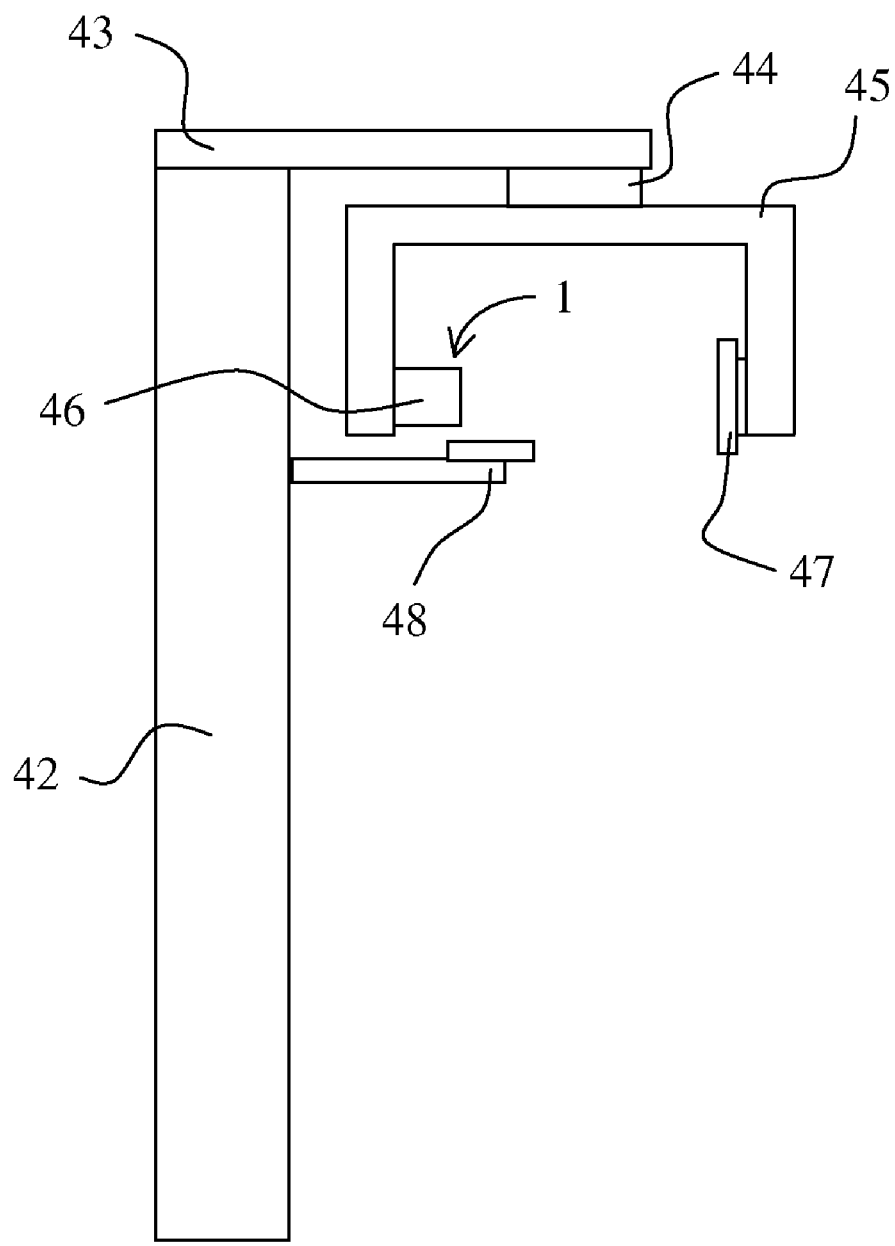

The collimator according to the current invention is primarily designed for use as a so-called primary collimator in a dental panoramic x-ray apparatus. A typical such apparatus is shown in FIG. 4, comprising a column-like body part (42) and a cantilever-type supporting element (43) mounted on the upper end of the body part (42), possibly pivotally so as to enable rotation of it with respect to the body part (42). At or near the end of said supporting element (43), an imaging arm often called a C-arm (45) is arranged for supporting an image data receiver (47) and an X-ray source (46). The mounting construction (44) for the C-arm (45) is designed to enable rotation of the C-arm (45) and horizontal movement of the rotation center of the C-arm (45). Attached to the column-like body (42) is arranged a patient support element (48). The apparatus may also be arranged to be used for e.g. cephalometric imaging by integrating a cephalometric imaging station to it (not shown in the Fig.), arranged at the end of a separate support arm mounted on the body part (42). The plate mechanism (1) is arranged within the cover of the x-ray source (46), as facing the image data receiver (47). The frame element (20) of the plate mechanism (1) according to the invention may be arranged to be a part of the x-ray tube housing such that, in view of FIG. 3a, for example, the first plate element (2) will be facing the x-ray source (46) and the second plate element (3) the patient/the image data receiver (47). Instead of being mounted on a column-like body part (42), the cantilever-type supporting element (43) may also be mounted on a wall or a ceiling.

The invention claimed is:

1. A device for limiting an x-ray beam of a dental extraoral imaging apparatus, said device comprising a plate mechanism (1) and a drive mechanism arranged to move at least one plate element (2,3) of said plate mechanism (1), characterized in that the plate mechanism (1) comprises a first plate element (2) including at least a first slot (12) for limiting the x-ray beam and a second plate element (3) including at least a second slot (13) for limiting the x-ray beam, said drive mechanism including an actuator (4) arranged to directly or indirectly move said first plate element (2) independently of the location of said second plate element (3) and said second plate element (3) being arranged to be moved solely by and dependent on the movements of said first plate element (2), and that at least portions of said first and second plate elements (2, 3) are arranged to be movable on different planes so as to enable positioning of said first and second slots (12, 13) of the first and second plate elements (2, 3) in an overlapping position with respect to each other so as to form an aperture for limiting the x-ray beam, the form of said aperture then being limited by both the first slot (12) and the second slot (13).

2. A device according to claim 1, characterized in that such an operation range has been arranged to the plate mechanism (1) within which said first plate element (2) is arranged to be movable back and forth in one dimension and said second plate element (3) is arranged to be movable as driven by said first plate element (2) in both of these directions.

3. A device according to claim 1, characterized in that such means has been arranged to the plate mechanism (1), which will cause a direct or indirect contact between the first and second plate elements (2, 3) when the first plate element (2) is driven towards an end of the operation range of the plate mechanism (1) in said dimension of movement arranged to the mechanism, and wherein dimensions and construction of the parts of the plate mechanism (1) have been arranged such that when the direction of movement of the first plate element (2) is reversed, there is a distance within which the first plate element (2) alone will move before such a direct or indirect contact is created between said first and second plate elements (2, 3) that will cause the second plate element (3) to move in the direction of movement of the first plate element (2).

4. A device according to claim 1, characterized in that the shapes of the first and second plate elements (2, 3) are arranged to be at least substantially flat and to be movable back and forth in one dimension but on different planes.

5. A device according to claim 1, characterized in that the first and second plate elements (2, 3) are arranged to be supported by a frame element (20) via constructions, which enable displacement of said plate elements (2, 3) with respect to said frame element (20).

6. A device according to claim 5, characterized in that said frame element (20) includes an elongated hole (21) through which supporting means (7,8) for both said first and second plate elements (2,3) are arranged to extend.

7. A device according to claim 1, characterized in that said first plate element (2) is connected to said drive mechanism via a connection element (7).

8. A device according to claim 1, characterized in that said plate mechanism (1) is supported by a frame element (20) whereto at least one groove, rail or a corresponding guide track (21, 22) has been arranged and that said first and second plate elements (2, 3) of the plate mechanism (1) are provided with means (7, 8) arranged to fit to said guide track (21, 22) such that movement of said plate elements (2, 3) along said guide track (21,22) is enabled.

9. A device according to claim 8, characterized in that means (7, 8) arranged to fit to said guide track (21, 22) to allow movement of the second plate element (3) along the guide track (21,22) comprises two elements (9) which are arranged of a distance further apart from each other than is the dimension of the first plate element (2) in the direction of said guide track (21,22).

10. A device according to claim 9, characterized in that, regarding the dimension the first and second plate elements (2, 3) are arranged to be moved, said second plate element (3) is arranged to be wider than said first plate element (2) and said first plate element (2) is arranged to be moved within the width covered by the second plate element (3).

11. A device according to claim 1, characterized in that said first slot (12) of the first plate element (2) is arranged to be rectangular and its horizontal dimension to be substantially smaller than its vertical dimension, and its vertical dimension to be at least as much as that of the highest portion of the second slot (13) of the second plate element (3), or at least as much as that of the highest slot (3) of the second plate element (3).

12. A device according to claim 1, characterized in that said second slot (13) is arranged to include at least two portions of different heights and/or at least two portions arranged on different horizontal levels and/or at least two rectangular slots of different heights and/or at least two rectangular slots arranged on different horizontal levels, or any combination of these comprising at least one slot including at least two portions of different heights and at least one rectangular slot.

13. A device according to claim 1, characterized in that such a range for the first plate element (2) is arranged within which it may be moved, with respect to the second plate element (3), without causing such a contact being made between the first and second plate elements (2, 3) that the second plate element (3) would begin to move in the direction of movement of the first plate element (2), which range is arranged to be at least as long as is the width of the second slot (13) of the second plate element (3), or the distance between the outermost slots (13) of the second plate element (3).

14. Dental panoramic x-ray imaging apparatus including a body part (42) for a cantilever-type supporting element (43) mounted at the end of said body part (42), in which at or near the end of said supporting element (43) is arranged an imaging arm 45 for supporting an image data receiver (47) and an X-ray source (46), characterized in that the apparatus includes a plate mechanism device (1) according to claim 1 arranged for limiting the x-ray beam produced by said x-ray source (46).

15. Apparatus according to claim 14, characterized in that said plate mechanism (1) is arranged fixed to a housing of said x-ray source (46).

16. A method for limiting an x-ray beam in connection with dental extra oral imaging in order to expose a desired portion of the object to be imagined only, in which method at least one plate element (2, 3) of a plate mechanism (1) limiting the x-ray beam is moved by means of a drive mechanism including an actuator (4) so as to produce a beam of a specific form, characterized in that two plate elements (2, 3) are used, out of which the first plate element (2) includes a first slot (12) and the second plate element (3) includes a second slot (13), and the plate elements (2, 3) are moved by use of the same single actuator (4) in such a manner that the first plate element (2) is moved by said drive mechanism and independently of location of said second plate element (3), whereas said second plate element (3) is moved as dependent of the location of the first plate element (2) via movements of said first plate element (2) to such positions within the operation range of the plate mechanism that said first and second slots (12,13) of the plate elements (2, 3) overlap to form an aperture to limit the x-ray beam, the form of said aperture thus becoming defined by the combined aperture formed by said first and second slots (12, 13) of the first and second plate elements (2, 3).

17. A method according to claim 16, characterized in that said first plate element (2) is moved in one dimension and said second plate element (3) is moved by said first plate element (2) such that at least part of the second plate element (3) moves on a different but parallel plane than said first plate element (2).

18. A method according to claim 16, characterized in that said second plate element (3) is first driven to its desired location by moving said first plate element (2) and said first plate element (2) is then driven to its desired location by the action of said drive mechanism.

* * * * *